United States Patent [19]

Pfister

[11] 4,353,922

[45] Oct. 12, 1982

[54] ANTICHOLINERGIC BRONCHODILATORS

[75] Inventor: Jurg R. Pfister, Los Altos, Calif.

[73] Assignee: Syntex (U.S.A.) Inc., Palo Alto, Calif.

[21] Appl. No.: 243,674

[22] Filed: Mar. 13, 1981

[51] Int. Cl.³ .................. C07D 487/08; A61K 31/40
[52] U.S. Cl. ................................ 424/274; 546/272;
564/210; 549/525; 549/546; 549/513
[58] Field of Search .................. 260/326.25, 326.32;
424/274; 546/272

[56] References Cited

U.S. PATENT DOCUMENTS 4,273,778 6/1981 Hadley et al. ................ 260/326.25

Primary Examiner—Mary C. Lee
Attorney, Agent, or Firm—James M. Kanagy; Alan M. Krubiner; Tom M. Moran

[57] ABSTRACT

Compounds of the formula

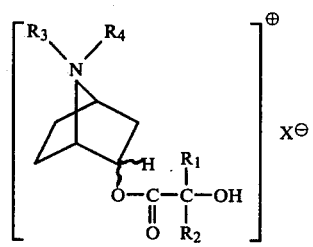

wherein the serrated lines denote both endo and exo forms; $R_1$ and $R_2$ are the same or different and are $C_1$ to $C_6$ alkyl, $C_5$ or $C_6$ cycloalkyl, $C_5$ or $C_6$ cycloalkenyl, phenyl optionally substituted with $C_1$ to $C_6$ alkyl, $C_1$ to $C_6$ alkoxy or halo, or 5 or 6 membered heterocyclic aryl wherein the heteroatom is oxygen, nitrogen or sulfur; $R_3$ is a $C_1$ to $C_6$ alkyl radical; $R_4$ and X are optionally present, and when present $R_4$ is a $C_1$ to $C_6$ alkyl radical or hydrogen and X is an inorganic or organic anion which forms a pharmaceutically acceptable salt. Methods for preparing these compounds are also disclosed. The compounds of the present invention are useful as anticholinergic agents.

13 Claims, No Drawings

ANTICHOLINERGIC BRONCHODILATORS

BACKGROUND OF THE INVENTION

1. Field of the Invention

This invention relates to novel azabicycloheptyl glycolates, their pharmaceutically acceptable salts, novel intermediates, and to methods for preparing these compounds. More particularly this invention relates to α-disubstituted azabicycloheptyl glycolates and their pharmaceutically acceptable salts; to novel intermediates; to pharmaceutical compositions comprising one or more of the above compounds; to a method for achieving anticholinergic effects in mammals through administration of these compounds; and to processes for preparing these compounds.

2. Prior Art

Azabicyclooctyl and azabicyclononyl benzilates and substituted acetates are known to have anticholinergic activity.

A process for preparing quinuclidinyl and tropinyl esters of benzilic acid is disclosed in U.S. Pat. No. 3,252,981. The resulting compounds are stated to have anticholinergic effects. Bis-(p-chlorophenyl)acetate wherein the various alcohols used include quinuclidinol, and having anticholinergic activity, are set out in U.S. Pat. No. 3,821,248. Isoquinuclidinol condensed with benzilic acid or substituted acetic acid and having anticholinergic activity are given in U.S. Pat. No. 3,118,896 and British Pat. No. 754,021-Q respectively.

Examples of substituted azabicyclononyl acetates having anticholinergic activity are given in the following patents: JA 7,308,635-R; JA 7,308,634-R; German Pat. Nos. 1,166,787; 1,207,395; and 2.123,314-Q; Belgium Pat. No. 623,889; and Netherlands Pat. No. 7,007,815 Q.

The compounds of this invention differ from those disclosed above in that the alcohol moiety is a azabicycloheptanol or a quaternary ammonium salt thereof. None of these references discloses the subject compounds, processes for their preparation or indicates that they may have anticholinergic activity.

SUMMARY

Compounds of the present invention are represented by the following generic formula

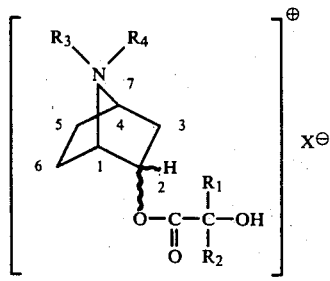

wherein the serrated lines denote both endo and exo forms; $R_1$ and $R_2$ are the same or different and are $C_1$ to $C_6$ alkyl, $C_5$ or $C_6$ cycloalkyl, $C_5$ or $C_6$ cycloalkenyl, phenyl optionally substituted with $C_1$ to $C_6$ alkyl, $C_1$ to $C_6$ alkoxy or halo, or 5 or 6 membered heterocyclic aryl wherein the heteroatom is oxygen, nitrogen or sulfur; $R_3$ is a $C_1$ to $C_6$ alkyl radical; $R_4$ and X are optionally present, and when present $R_4$ is a $C_1$ to $C_6$ alkyl radical or hydrogen and X is an inorganic or organic anion which forms a pharmaceutically acceptable salt.

Novel compounds which are useful as intermediates in the processes for preparing these compounds are also disclosed.

A third aspect is the novel processes for preparing these compounds. The process comprises converting a cyclohexenyl carbonyl chloride to an azide intermediate, adding trifluoroacetic acid to form an acetamide and then alkylating the nitrogen. The double bond is then converted to an epoxide with a peroxyacid after which the trifluoracetyl protecting group is removed whereupon the secondary nitrogen is made to undergo an intramolecular reaction with the epoxide to form the endo-azabicycloheptanol. The exo-form is made by refluxing the endo-compound with an alkali metal in an alcohol/xylene solution doped with a ketone. Once the endo- or exo-bicyclo amine alcohol has been formed, transesterification with the appropriate α-disubstituted glycolate provides the azabicycloheptyl glycolate compound. Quaternary amonium salts are prepared by the addition of acid or by alkylation of the nitrogen. Alternatively formula 1 type compounds can be prepared from a quaternized azabicycloheptanol by condensing such an alcohol with a α-disubstituted glycolic acid or by transesterification with an alkyl α-disubstituted glycolate.

Another aspect of the invention is a pharmaceutical composition which comprises at least one compound of the invention in combination with one or more pharmaceutically acceptable excipients.

Still another aspect of this invention is a method for achieving anticholinergic effects in mammals which method comprises administering orally, parenterally or by inhalation, an effective amount of one or more of the azabicycloheptyl glycolate compounds or a pharmaceutically acceptable salt thereof of this invention, neat or in a suitable pharmaceutical composition.

The compounds, compositions and methods of the present invention disclosed above will become more readily apparent from the following description.

DETAILED DESCRIPTION OF THE INVENTION

As used in the specification and the appended claims, the following terms have the meanings indicated.

The 2-hydroxyl of the azabicycloheptanol may be in either of two positions relative to the cyclohexane portion of the azabicyclo structure. When the hydroxyl is oriented perpendicular to the plane of the cyclohexane ring it is said to be in an axial position and compounds of that form are denoted by use of the prefix "endo". When the hydroxyl parallels the plane of the cyclohexane ring it is said to be in an equatorial position and compounds with that steric orientation carry the prefix "exo". Both steric forms are being claimed herein. To exemplify this fact, where necessary, serrated lines are used for the 2-position ring substituents to indicate that both endo and exo forms of the compounds are being described in that instance.

The term "$C_1$ to $C_6$ alkyl" refers to straight or branched chain, monovalent substituents consisting solely of carbon and hydrogen, containing no unsaturation and having 1 to 6 carbon atoms. Examples of such alkyl groups are methyl, ethyl, n-propyl, i-propyl, n-butyl, t-butyl and the like. The term "$C_1$ to $C_6$ alkoxy" refers to the above disclosed alkyl groups linked through an ether linkage, having the free valence from the ether oxygen. Examples of such groups include methoxy, ethoxy, n-propoxy, i-propoxy, n-butoxy, t-butoxy and the like. The term "C₄ to C₆ cycloalkyl" refers to a 4, 5 or 6 membered monovalent ring containing only hydrogen and carbon that is fully saturated such as is exemplified by cyclobutyl, cyclopentyl and cyclohexyl. "C₅ to C₆ cycloalkenyl" differs from the above cycloalkyl by having in the ring at least one unsaturated bond. Such includes 1-, 2-, or 3-cyclopentenyl, 1-, 2-, or 3-cyclohexenyl, 1,4-cyclohexadienyl, 1,3-cyclopentadienyl, and the like.

The term "heterocyclic aryl, wherein the heteroatom is oxygen, nitrogen and sulfur" is intended to mean the heterocyclic compounds of aromatic character containing, in addition to the heteroatom, 4 or 5 carbon atoms in the ring. Examples of these radicals are: pyrroyl, for example, 2- or 3-pyrrolyl; pyridyl, for example, 2-, 3- or 4-pyridyl; thienyl, for example, 2- or 3-thienyl; and furyl, for example, 2-furyl or 3-furyl.

"Phenyl optionally substituted with C₁ to C₆ alkyl, C₁ to C₆ alkoxy or halo" is intended to include unsubstituted phenyl, monosubstituted phenyl and polysubstituted phenyl. Such include: methylphenyl, for example, 2- or 3-methylphenyl; dimethylphenyl, for example, 2,4- or 3,5-dimethylphenyl; methoxyphenyl, for example, 2- or 3-methoxyphenyl; dimethoxyphenyl, for example, 2,4- or 3,5-dimethoxyphenyl; halophenyl, for example, 4-chlorophenyl, or 4-bromophenyl; or dihalophenyl, for example, 2,4-dichlorophenyl or 2,4-dibromophenyl.

The term "halo" refers to fluoro, chloro, bromo and iodo when these atoms are covalently bonded to carbon. The term "halide" is used when these same atoms constitute the anion of a quaternary amine compound and refer to the fluoride, chloride, bromide and iodide ions.

The phrase "pharmaceutically acceptably salt" means any quaternary ammonium salt of the azabicycloheptyl glycolates described herein prepared by reaction of the amine with inorganic acids, organic acids or alkylating agents and which exhibit anticholinergic activity. Inorganic acids which form acceptable salts are, for example, hydrochloric acid, hydrobromic acid, sulfuric acid, nitric acid or phoshporic acid. Acceptable organic acids are, for example, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, pamoic acid, cinnamic acid, mandelic acid, methanesulfonic acid, ethanesulfonic acid, p-toluenesulfonic acid, benzenesulfonic acid and the like. Alkylating agents which may be used herein are, for example, methyl bromide, methyl chloride, methyl iodide, ethyl chloride, ethyl bromide, ethyl iodide, n-propyl bromide, n-propyl chloride, n-propyl iodide, isopropyl bromide, isopropyl chloride, n-butyl bromide, n-butyl chloride, methyl tosylate and the like.

"Azabicycloheptyl glycolates" means those compounds which are the condensation product of an azabicycloheptanol, either an exo-2 or an endo-2 alcohol, and an α-disubstituted glycolic acid or the transesterification product of such a heptanol and an alkyl α-disubstituted glycolate.

The term "α-disubstituted glycolic acid" refers to the derivatives of glycolic acid, 2-hydroxy acetic acid, wherein the two hydrogens of glycolic acid have been replaced by those radicals set out as R₁ and R₂ in the specification. When the phrase "alkyl α-disubstituted glycolate" is used it refers to those C₁ to C₆ alkyl esters of the aforedescribed α-disubstituted glycolic acids.

Compounds of formula I may exist in the endo-2-acetoxy or exo-2-acetoxy configuration as represented by formulas (2) and (3)

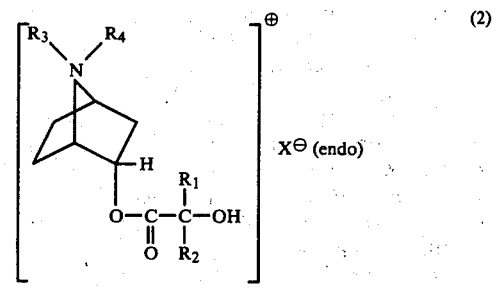

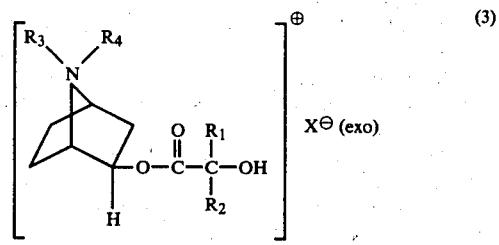

wherein R₁, R₂, R₃, R₄, and X are as defined above. This invention encompasses each of the endo or exo forms, alone or in combination.

Preferred compounds of the present invention are those wherein R₁ is phenyl, optionally substituted with a substituent selected from the group consisting of C₁ to C₄ alkyl, C₁ to C₄ alkoxy, chloro and bromo; R₂ preferably is the same as R₁ or is a C₅ or C₆ cycloalkyl or sulfur containing hetero aryl; R₃ is a C₁ to C₄ alkyl radical; and R₄ and X are present, R₄ being a C₁ to C₆ alkyl radical and X is methanesulfonate, benzenesulfonate, chloride or bromide.

Most preferred are those compounds of formula 2 wherein R₁ is phenyl; R₂ is phenyl, thienyl, cyclopentyl, cyclohexyl or isopropyl; R₃ is methyl; R₄ is hydrogen or methyl; and X is bromide or chloride.

Particularly preferred compounds of formula 2 are:
  endo-2-(2-hydroxy-2,2-diphenyl)acetoxy-7-methyl-7-azabicyclo-[2.2.1]heptane methyl bromide;
  endo-2-(2-hydroxy-2,2-diphenyl)acetoxy-7-methyl-7-azabicyclo-[2.2.1]heptane hydrochloride;
  endo-2-[2-hydroxy-2-phenyl-2-(thien-3-yl)]acetoxy-7-methyl-7-azabicyclo[2.2.1]heptane methyl bromide;
  endo-2-[2-hydroxy-2-phenyl-2-(thien-2-yl)]acetoxy-7-methyl-7-azabicyclo[2.2.1]heptane methyl bromide;
  endo-2-(2-cyclopentyl-2-hydroxy-2-phenyl)acetoxy-7-methyl-7-azabicyclo[2.2.1]heptane methyl bromide;
  endo-2-(2-cyclohexyl-2-hydroxy-2-phenyl)acetoxy-7-methyl-7-azabicyclo[2.2.1]heptane methyl bromide; and
  endo-2-(2-hydroxy-2-isopropyl-2-phenyl)acetoxy-7-methyl-7-azabicyclo[2.2.1]heptane methyl bromide.

In brief the reaction scheme for preparing the subject compounds proceeds from a cyclohexenyl carbonyl chloride which is converted to an azide intermediate, adding trifluoroacetic acid to form a protected secondary nitrogen, followed by alkylation of the nitrogen. The azabicycloheptyl ring structure is achieved by epoxidation of the ring double bond, removal of the trifluoracetyl protecting group and subsequent formation of the endo-2-azabicycloheptyl alcohol through an intramolecular reaction by the secondary nitrogen with the epoxide ring. The exo-form is made by refluxing the endo-compound with an alkali metal in an alcohol/xylene solution doped with a ketone. Once the endo- or exo-azabicycloheptyl alcohol has been formed, transesterification with the appropriate alkyl α-disubstituted glycolate provides the azabicycloheptyl glycolate compound. Salts are formed by conventional means to give the preferred compounds.

The compounds of formula 1 may be prepared by an alternative route. Once the endo- or exo-azabicycloheptanols have been formed they may be quaternized by means of an acid or alkyl halide and then esterified with a glycolic acid or alkyl glycolate. Also, when formula 1 compounds exist as the alkyl halide quaternary ammonium salt they may be converted to the corresponding alkyl nitrate quaternary ammonium salt using, for example, silver nitrate.

The compounds of the present invention are made by the following process depicted schematically:

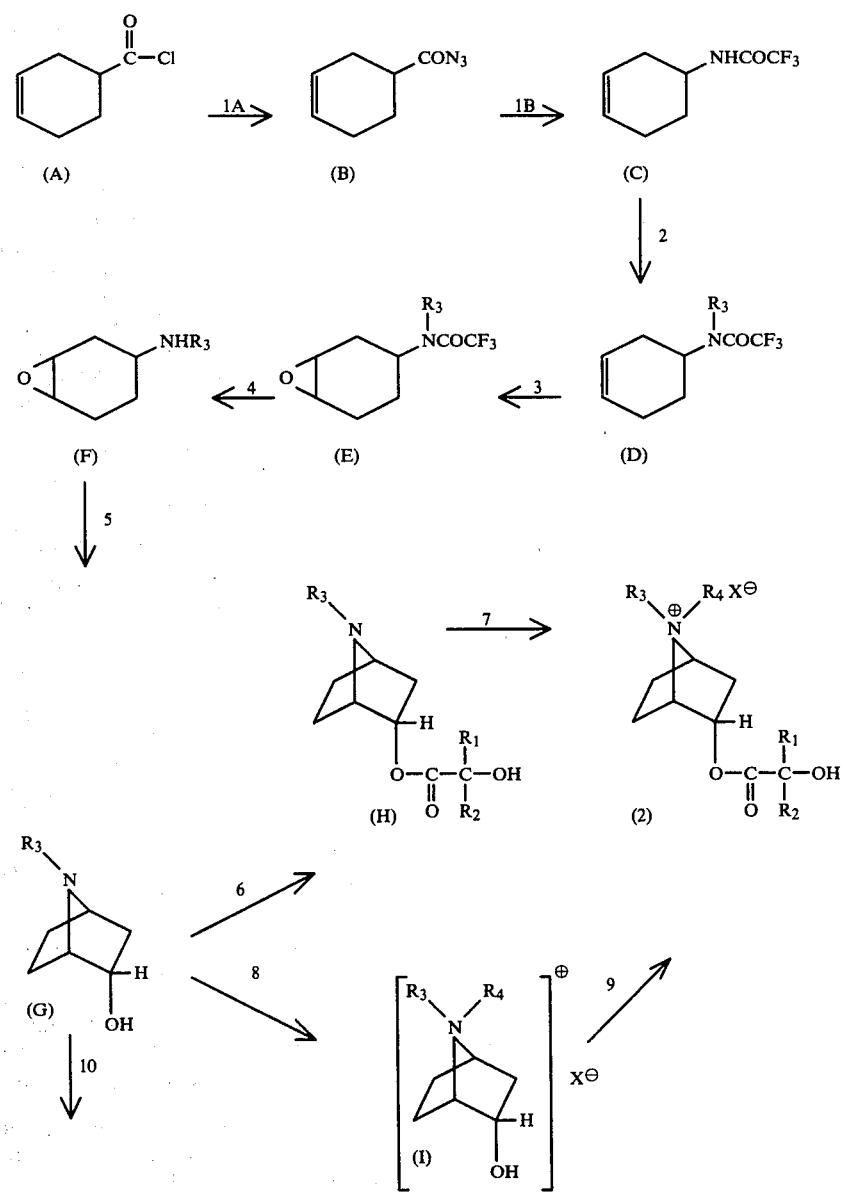

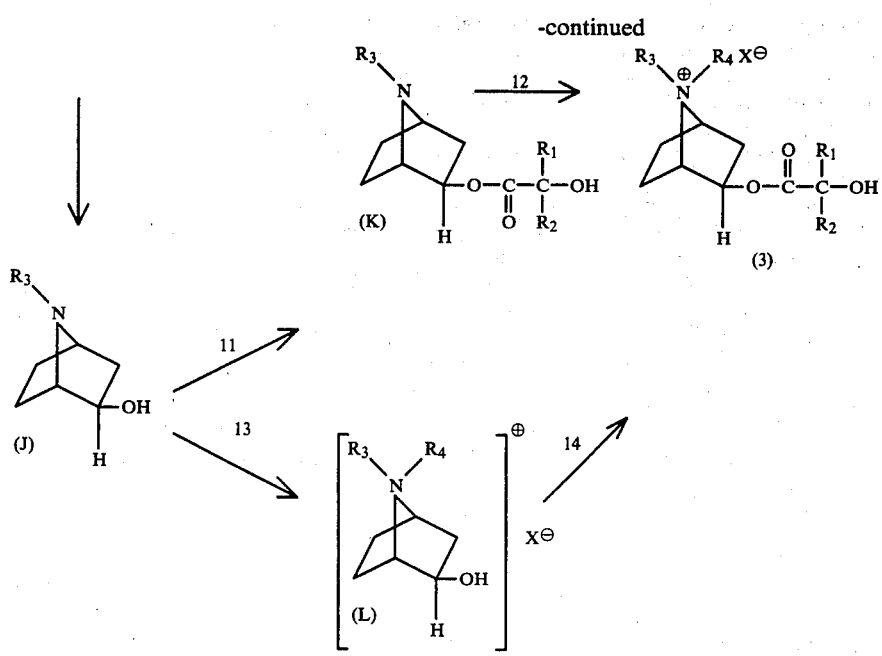

The initial reaction, as shown in step 1, involves the treatment of a cyclohexenyl acid halide, here 3-cyclohexenylcarbonyl chloride, with a slight molar excess of sodium azide in a two phase organic/water system with mixing, followed by heating to effect a Curtius type rearrangement to give an isocyanate followed by addition of trifluoroacetic acid with refluxing to achieve the N-trifluoroacetylamino compound. Formation of the acid azide is realized by dissolving the acid chloride (formula A) in an aprotic organic solvent, for example an halogenated hydrocarbon such as dichloromethane, along with a phase transfer catalyst such as tetrabutylammonium bromide, cooling the solution to −20° to 10° C., adding an aqueous solution of sodium azide and vigorously stirring the resulting two-phase system for one-half to 4 hours, typically about 2 hours, to afford the acid azide (formula B). The organic layer is then removed, washed and dried. Without further manipulation the dried organic layer is treated with trifluoroacetic acid slowly, and refluxed for several hours, typically about 6, after which the cooled solution is washed, dried and the solvent evaporated. The acetamide is further purified by low pressure distillation and crystallization from a nonpolar solvent such as hexane to give the 3-cyclohexenyltrifluoroacetamide (formula C).

Alkylation of the trifluoroacetamide follows commonly known procedures for such reactions. As practiced herein the amide and an excess of an alkyl halide, here exemplified by a methyl halide, are dissolved in dimethylformamide, the solution cooled to 0° and an alkali metal hydride added. After stirring the solution for a short time, preferably 1 hour, at a moderate temperature, typically room temperature, there is obtained the 3-cyclohexenylmethyl- trifluoroacetamide (formula D).

Formation of the epoxide (formula E) can be achieved by treating the N-methyltrifluoroacetamide, derivative (D), with a peroxyacid, for example, m-chloroperoxybenzoic acid. The reaction is carried out in an inert organic solvent such as a halogenated alkane, for example, dichloromethane, dichloroethane and the like, the reaction being conducted for a time and at a temperature sufficient to assure completeness of the reaction, typically 3–5 hours at room temperature.

Step 4 is a base-induced hydrolysis of the N-trifluoroacetyl protecting group. The reaction is carried out by adding an aqueous solution of a base such as potassium carbonate, sodium carbonate and the like, to a water miscible organic solvent for example methanol, ethanol, n-propanol or the like containing the compound of formula (E). Generally the resulting solution is stirred for several hours, preferably about 4 hours, at a temperature between 10°–40° C. but typically at room temperature.

Formation of the endo-2-azabicycloheptanol, formula (G), is achieved through an intramolecular opening of the epoxide by the alkyl (methyl)amino group. The reaction is heat-induced, being carried out under an inert atmosphere in an inert polar organic solvent, for example, dimethylformamide, dimethylacetamide, N-methylpyrrolidone, and the like. Typically the reaction is carried out under nitrogen at a temperature between 100°–200° C. for 24 to 72 hours, but preferably at a temperature of about 155°–160° C. for about 48 hours.

The exo-2- form of the azabicycloheptanol (formula J) can be prepared from the endo-2- form using the procedure of Aaron, et. al. in the Journal of Organic Chemistry, Vol. 31, p. 3502–3507 (1966). This method employs an alkali metal salt of an alcohol with a ketone catalyst under reflux to effect interconversion of the endo-2- to the exo-2- compound. Sodium or potassium metal in an inert solvent is added slowly to an alcohol such as n-butanol, n-pentanol or the like. A 10 fold excess of metal relative to the reactant is prepared in a solution containing twice as much alcohol as inert solvent. The reactant is then added to the solution along with a small amount of a ketone, for example cyclohexanone. Refluxing is carried out for several days, usually 48 hours.

Alternative paths can be used for converting compounds of formulas (G) and (J) to formulas (2) and (3) respectively. In one method the heptanol is first esterified using an α-disubstituted alkyl glycolate in the presence of a base catalyst and then quaternized. Alternatively, the azabicycloheptanols are first quaternized using an alkylating agent and then esterfied to give compounds of formulas 2 and 3.

Formation of the azabicycloheptyl glycolates from formulas (G) or (J) is preferably accomplished by base-catalyzed transesterification involving the azabicycloheptanol and an alkyl α-disubstituted glycolate. Transesterification is best achieved by dissolving an appropriate alkyl (preferably methyl) glycolate ester and the amino alcohol in a non-polar inert organic solvent such as hexane, heptane, toluene and the like, containing a catalytic amount of base, such as sodium hydride or sodium methoxide, and refluxing the solvent through a molecular sieve for an appropriate time, usually about 12-16 hours.

After isolation and purification of formulas (H) and (K) type compounds they can be converted to an pharmaceutically acceptable salt by generally known methods. Typically the azabicycloheptyl glycolate is dissolved in a solvent such as acetone, 2-butanone, methanol, ethanol and the like, to which a compound capable of forming a salt is then added. This same procedure can be used for quaternizing the amino heptanols of formulas (I) and (L).

Generally a molar equivalent and preferably an excess of the salt forming compound relative to the amine, is added to the azabicycloheptyl glycolate or azabicycloheptanol containing solution. Alkyl halide salts are formed by adding the appropriate alkyl halide to a solution of the azabicycloheptyl or alcohol ester at a moderate temperature, typically ambient, and the reaction allowed to proceed for up to 24 hours. Acid salts of the azabicycloheptyl glycolate are made by adding an excess of the acid in a solvent to a room temperature solution of a glycolate and collecting the formed crystals by filtration.

The alternative method for converting compounds of formulas (G) and (J) to formulas (2) and (3) involves first preparing the quaternary amine compounds of formulas (I) and (L) using an alkyl halide and then esterifying the quaternary amine with an α-disubstituted glycolic acid in the presence of a dehydrating agent.

Formation of azabicycloheptanol alkyl halide quaternary ammonium salts follows the same procedure used for converting azabicycloheptyl glycolates to this salt form set out above.

The preparation of esters from the azabicycloheptanol alkyl halide salts can be accomplished by combining a molar excess of an α-disubstituted glycolic acid, relative to the azabicycloheptanol, in a solvent which is also a dehydrating agent, for example trifluoroacetic anhydride. This reaction can be carried out at a temperature of between about 0° and 50° C. but is conventionally carried out a room temperature. The first step of the reaction scheme involves dissolving the α-disubstituted glycolic acid in the solvent and allowing this solution to stand for about 15 to 60 minutes, preferably about 30 minutes before adding the quaternized azabicycloheptanol. After this preliminary solvent/acid equilibration period, the quaternized azabicycloheptanol is added with stirring which is continued for up to about 3 hours, but preferably about 1 hour.

Exchanging the formula 1 halide anion for a nitrate anion is realized by the addition of an equimolar amount of silver nitrate to a solution containing a formula 1 compound wherein $R_4$ is an alkyl group.

The compounds of formula (1) may be prepared by:
(a) converting a compound of the formula

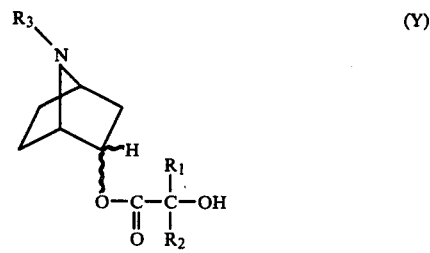

(Y)

wherein $R_1$, $R_2$, and $R_3$ are defined above, to an pharmaceutically acceptable salt by treating a compound formula Y with an alkylating agent $R_4X$, or an inorganic acid or an organic acid, HX;

(b) converting a compound of the formula

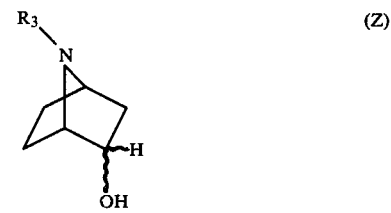

(Z)

wherein $R_3$ is defined above, to a quaternary amine by treating a compound of formula (Z) with an alkylating $R_4X$ agent and then reacting said quaternery amine with an α-disubstituted glycolic acid in the presence of a dehydrating agent; or (c) converting a compound of formula 1 wherein $R_4$ is $C_1$ to $C_6$ alkyl and X is halide to one wherein X is nitrate by treating said compound with silver nitrate.

The compounds of the invention are primarily antagonists of acetylcholine and effective bronchodilators, particularly for asthma in humans. They are several times more effective per unit dose than other known anticholinergics and are 3 to 5 times longer lasting in their activity. The compounds of this invention are typically administered in dosages of about from 0.0001 to 0.1 mg per kg of body weight. A preferable dose for a human, given by inhalation, would be approximately 0.0025 mg per kg of body weight. The precise effective dosage will of course, vary depending upon the mode of administration, the condition being treated, and the host. Where the compounds are used as pulmonary anticholinergics in mammals they are typically administered either orally, intravenously or by inhalation.

The compounds of the present invention can be administered in a wide variety of dosage forms, either alone or in combination with other pharmaceutically compatible medicaments, or in the form of pharmaceutical compositions suited for oral, parenteral or aerosol administration. The compounds are typically administered as pharmaceutical compositions consisting essentially of the compounds of the invention and a pharmaceutical carrier. Generally the pharmaceutical composition will contain about 0.01 to 15% by weight of at least one compound on this invention with about 99.0 to 80% of the carrier. Preferably the drug will be present in an amount of between 0.1 to 1.0%. The pharmaceutical carriers can be either a solid or a liquid in which the compound is dissolved, dispersed or suspended, and can optionally contain small amounts of preservatives and- /or pH-buffering agents. Suitable preservatives which can be used include, for example, benzyl alcohol and the like. Suitable buffering agents include, for example, carbonates, acetates, phosphate salts and the like.

The liquid compositions can, for example, be in the form of solutions, emulsions, suspensions, syrups, or elixirs and optionally can contain small quantities of preservatives and/or buffering agents, and preferably contain the therapeutic agents in convenient unit dosage.

The solid compositions can take the form of tablets, powders, capsules, pills and the like, preferably in unit dosage forms for simple administration and precise dosages. Suitable solid carriers include, for example, pharmaceutical grades of starch, lactose, sodium saccharine, sodium bisulfite and the like.

The compounds of formula 2 and 3 can be administered as racemic mixtures or they can be administered as resolved enantiomers or optical isomers. In some instances, one enantiomer or optical isomer may exhibit a greater anticholinergic effect than does the corresponding enantiomer or optical isomer.

The compounds of formula 2 and 3 or their precursors possess a chiral center at position 2 of the azabicycloheptyl ring. Accordingly, when applicable, compounds disclosed in this invention may be prepared in either an optically active form or as a racemic mixture. Unless otherwise specified, where applicable, the compounds described herein are in the racemic form. However, the scope of the subject invention is not to be considered limited to the racemic form, but to encompass the individual optical isomers of all the optically active compounds of the present invention.

Where desired the individual diastereomeric and optically isomeric compounds can be isolated by conventional separation and purification procedures in the case of diastereomers and by conventional resolution procedures in the case of optical isomers. Optimum physical or physical-chemical separation procedures and resolution procedures can be obtained by routine trial and error procedures well within the scope of those skilled in the art.

A further understanding of the invention can be had from the following non-limiting Preparations and Examples. As used herein above, and below, unless expressly stated to the contrary, all temperatures and temperature ranges refer to the Centigrade system and the terms ambient or room temperature refer to about 20° C. The term "percent" or "(%)" refers to weight percent and the term "mole" and "moles" refers to gram moles. The term "equivalent" refers to a quantity of reagent equal in moles to the moles of the preceding or succeeding reactant recited in that Preparation or Examples in the terms of moles of finite weight or volume. As noted earlier, compounds having asymmetric centers and optical activity are isolated in their racemic form (±) unless otherwise indicated.

PREPARATION 1

This preparation illustrates the conversion of 3-cyclohexenylcarbonyl chloride to the trifluoroacetamide formula (C) by way of formula (B) which was not isolated.

To an ice-cooled solution of 90.5 g 3-cyclohexenylcarbonyl chloride and 0.5 g tetrabutylammonium bromide in 1 liter of dichloromethane was added a solution of 50 g sodium azide in 150 ml water. The resulting two-phase system was stirred vigorously at 0° for 2 hours. The organic phase was separated, washed with water, dried over magnesium sulfate, and filtered. The acid azide was not isolated from this filtrate but was converted to the trifluoroacetamide by adding 65 ml of trifluoroacetic acid, slowly, to the filtrate and refluxing the resulting solution for 6 hours. The cooled solution was washed with sodium bicarbonate, dried over magnesium sulfate, filtered, and evaporated to dryness. The solid residue was subjected to bulb-to-bulb distillation to give 105.9 g 3-cyclohexenyltrifluoroacetamide, m.p. 62°–63°, after recrystallization from hexane.

PREPARATION 2

This preparation illustrates the conversion of the trifluoroacetamide derivative, formula (C), to the N-methyltrifluoroacetamide derivative, formula (D).

A solution of 105.9 g 3-cyclohexenyltrifluoroacetamide and 106 ml methyl iodide in 675 ml of dimethylformamide was cooled to 0°. 29.6 g of sodium hydride was added in portions. After stirring at room temperature for 1 hour, the reaction mixture was diluted with water (ca. 4 liters) containing acetic acid (50 ml), and extracted with ether. The organic phase was washed with water, dried over magnesium sulfate, filtered, and concentrated by distillation at normal pressure on a steam bath. The residue was distilled at the aspirator to give 101.7 g 3-cyclohexenylmethyltrifluoroacetamide, b.p. 107°–109° (12 mm Hg).

PREPARATION 3

Preparation 3 illustrates the epoxidation of the 3-cyclohexenylmethyltrifluoroacetamide, formula (D), to give the corresponding epoxide, formula (E).

To a solution of 101.6 g 3-cyclohexenylmethyltrifluoroacetamide in 2 liters of dichloromethane, cooled in an ice bath, were added 117 g of m-chloroperoxybenzoic acid in portions. After stirring for 4 hours at room temperature, excess peracid was destroyed with potassium iodide in water, followed by sodium sulfite. The mixture was separated, the organic phase washed with sodium bicarbonate, dried over magnesium sulfate, filtered and evaporated to leave 107.3 g 4-trifluoroacetylmethylaminocyclohexane-1.2-oxide as an oily mixture of the two stereoisomers.

PREPARATION 4

Wherein is illustrated the base-induced hydrolysis of the N-trifluoroacetyl group of the compound of formula (E) to give the compound of formula (F).

To a solution of 107.3 g of 4-trifluoroacetylmethylaminocyclohexane-1.2-oxide in 300 ml of methanol was added a solution of 84.5 g of potassium carbonate in 300 ml of $H_2O$ and the resulting mixture was stirred at room temperature for 5 hours. Most of the methanol was removed under vacuum, and the residue was extracted with ether in a continuous extractor for 48 hours. The ether phase was dried over potassium carbonate, filtered, and evaporated to afford 40.9 g of 4-methylaminocyclohexane-1.2-oxide as a brown oil.

PREPARATION 5

This preparation illustrates the conversion of epoxide of formula (F) through intramolecular opening of the epoxide by nitrogen to give the compound of formula (G).

A solution of 40.9 g of 4-methylaminocyclohexane-1.2-oxide in 400 ml of N-methylpyrrolidone was heated under nitrogen at 155°–160° C. in an oil bath for 48 hours. The reaction mixture was distilled at the aspirator, and the distillate was acidified with cncentrated hydrochloric acid. The N-methylpyrrolidone was distilled off, the residue dried under oil pump vacuum at 80° and crystallized from methanol/ethyl acetate to give 23.4 g of endo-7-methyl-7-azabicyclo[2.2.1]heptan-2-ol hydrochloride, m.p. 261°–262°. The free base was obtained from the hydrochloride in the usual fashion, m.p. 47°–49° after sublimation.

PREPARATION 6

This preparation illustrates the the interconversion of an endo-2-azabicycloheptanol, formula (G), to the corresponding exo-2- form, formula (J).

Normal pentanol (500 ml) was added slowly with stirring to 35 g of potassium in 300 ml of xylene in a flask equipped with a reflux condensor and drying tube. When all the potassium had reacted, 10 g of endo-7-methyl-7-azabicyclo[2.2.1]heptan-2-ol, in 20 ml of xylene, and 4 ml of cyclohexanone were added. The mixture refluxed with stirring for 2 days. The total mixture was cooled, diluted with 50 ml of water, then acidified to pH 1 with concentrated hydrochloric acid. The organic phase was separated and extracted with three 50 ml portions of 6 N HCl. The aqueous phases were combined, treated with potassium hydroxide pellets to pH 14, and then extracted with three 100 ml portions of chloroform. The combined chloroform extract was dried over sodium carbonate and concentrated to give exo-7-methyl-7-azabiclo[2.2.1]heptan-2-ol.

PREPARATION 7

This preparation illustrates the conversion of formula (G) or (J) type compounds to the quaternary amino alcohols of formulas (I) or (L) respectively.

A solution of the endo-7-methyl-7-aza-bicyclo[2.2.1]heptan-2-ol and a slight molar excess of methyl bromide in 2-butanone was left at room temperature for 20 hours. The crystalline reaction product was isolated by suction filtration and recrystallized from methanol/ethyl acetate to afford endo-7-methyl-7-azabicyclo[2.2.1]heptan-2-ol methyl bromide.

Other amino alcohols of formulas (G) and (J) may be converted to corresponding quaternary amino alcohols utilizing this method.

PREPARATION 8

The esterification of formula (I) or (L) quaternary amino alcohols to give formula (2) to (3) type compounds is illustrated in this preparation.

A solution of 2.28 g of benzilic acid in 12 ml of trifluoroacetic anhydride was left at room temperature for 30 minutes. After adding 2.22 g of endo-7-methyl-7-azabicyclo[2.2.1]heptanol-2-ol, the reaction mixture was stirred at room temperature for one hour and then evaporated to dryness. The residue was dissolved in water, the aqueous solution washed with ether, saturated with sodium bromide, and extracted with ethyl acetate in a continious extractor for 24 hours. The solvent was removed in vacuo and the residue crystallized from methanol/2-butanone to give endo-2-(2-hydroxy-2,2-diphenyl)acetoxy-7-methyl-7-azabicyclo[2.2.1]-heptane methyl bromide, m.p. 256°–257° C.

Using this procedure other quaternary amino alcohols of formulas (I) and (L) may be converted to compounds of formula 1.

EXAMPLE I

This example illustrates the transesterification reaction by which can be obtained compounds of formula (H) and (K) from compounds of formula (G) and (J) respectively.

A mixture of 2.1 g methyl benzilate, 1.0 g of endo-7-methyl-7-azabicyclo[2.2.1]heptan-2-ol, 20 mg of sodium hydride, and 60 ml of n-heptane was refluxed through 4A molecular sieves for 16 hours. After cooling, the reaction mixture was diluted with ether and washed with water. The organic phase was extracted twice with 5% citric acid solution, and the basified aqueous phase was extracted with ether to give 2.0 g of endo-2-hydroxydiphenylacetoxy-7-methyl-7-azabicyclo[2.2.1]-heptane as an oil.

Using the above procedures, but substituting the appropriate α-disubstituted methyl glycolate and azabicycloheptanol, there may be prepared the following compounds:

endo-2-(2-hydroxy-2,2-diphenyl)acetoxy-7-methyl-7-azabicyclo-[2.2.1]heptane;

endo-2-[2-hydroxy-2-phenyl-2-(thien-3-yl)]acetoxy-7-methyl-7-azabicyclo[2.2.1]heptane;

endo-2-(2-cyclopentyl-2-hydroxy-2-phenyl)acetoxy-7-methyl-7-azabicyclo[2.2.1]heptane;

endo-2-(2-cyclohexyl-2-hydroxy-2-phenyl)acetoxy-7-methyl-7-azabicyclo[2.2.1]heptane;

endo-2-(2-hydroxy-2-isopropyl-2-phenyl)acetoxy-7-methyl-7-azabicyclo[2.2.1]heptane;

endo-2-[2-hydroxy-2-phenyl-2-(4-chlorophenyl)]-acetoxy-7-methyl-7-azabicyclo[2.2.1]heptane;

endo-2-[2-hydroxy-2-phenyl-2-(thien-2-yl)]acetoxy-7-methyl-7-azabicyclo[2.2.1]heptane;

endo-2-[2-hydroxy-2-phenyl-2-(4-methylphenyl)]-acetoxy-7-methyl-7-azabicyclo[2.2.1]heptane;

endo-2-(2,2-dicyclopentyl-2-hydroxy)acetoxy-7-methyl-7-azabicyclo[2.2.1]heptane;

endo-2-[2-hydroxy-2-cyclopentyl-2-(3-methylphenyl)]-acetoxy-7-methyl-7-azabicyclo[2.2.1]heptane;

endo-2-[2-hydroxy-2-phenyl-2-(pyrrol-3-yl)]acetoxy-7-methyl-7-azabicyclo[2.2.1]heptane;

endo-2-[2-(fur-2-yl)-2-hydroxy-2-phenyl]acetoxy-7-methyl-7-azabicyclo[2.2.1]heptane;

endo-2-[2-hydroxy-2,2-bis(4-chlorophenyl)]acetoxy-7-methyl-7-azabicyclo[2.2.1]heptane;

endo-2-[2-hydroxy-2,2-bis(4-methylphenyl)]acetoxy-7-methyl-7-azabicyclo[2.2.1]heptane;

endo-2-[2-hydroxy-2-phenyl-2-(cyclopent-2-enyl)]-acetoxy-7-methyl-7-azabicyclo[2.2.1]heptane;

endo-2-[2-hydroxy-2-cyclopentyl-2-(4-chlorophenyl)]-acetoxy-7-methyl-7-azabicyclo[2.2.1]heptane;

endo-2-[2-hydroxy-2-isopropyl-2-(4-chlorophenyl)]-acetoxy-7-methyl-7-azabicyclo[2.2.1]heptane;

endo-2-[2-hydroxy-2-cyclohexyl-2-(4-methylphenyl)]-acetoxy-7-methyl-7-azabicyclo[2.2.1]heptane;

exo-2-hydroxydiphenylacetoxy-7-methyl-7-azabicyclo[2.2.1]heptane;

exo-2-[2-hydroxy-2-phenyl-2-(thien-3-yl)]acetoxy-7-methyl-7-azabicyclo[2.2.1]heptane;

exo-2-(2-cyclopentyl-2-hydroxy-2-phenyl)acetoxy-7-methyl-7-azabicyclo[2.2.1]heptane;

exo-2-(2-cyclohexyl-2-hydroxy-2-phenyl)acetoxy-7-methyl-7-azabicyclo[2.2.1]heptane;

exo-2-(2-hydroxy-2-isopropyl-2-phenyl)acetoxy-7-methyl-7-azabicyclo[2.2.1]heptane;
exo-2-[2-hydroxy-2-phenyl-2-(4-chlorophenyl)]-acetoxy-7-methyl-7-azabicyclo[2.2.1]heptane;
exo-2-[2-hydroxy-2-phenyl-2-(thien-2-yl)]acetoxy-7-methyl-7-azabicyclo[2.2.1]heptane; and
exo-2-[2-hydroxy-2-phenyl-2-(4-methylphenyl)]-acetoxy-7-methyl-7-azabicyclo[2.2.1]heptane.

EXAMPLE 2

This preparation sets out a method whereby the azabicycloheptyl glycolates of Example 1 may be converted to an alkyl halide quaternary ammonium salt, exemplified by the methyl bromide salt.

A solution of 500 mg of endo-2-(2-hydroxy-2,2-diphenyl)acetoxy-7-methyl-7-azabicyclo[2.2.1]heptane and 500 mg of methyl bromide in 20 ml of 2-butanone was left at room temperature for 20 hours. The crystalline reaction product was isolated by suction filtration and recrystallized from methanol/ethyl acetate to afford 560 mg of endo-2-(2-hydroxy-2,2-diphenyl-)acetoxy-7-methyl-7-azabicyclo[2.2.1]heptane methyl bromide, m.p. 256°–257°.

Following the above procedure but substituting the appropriate azabicyclo[2.2.1]heptyl glycolate there may be prepared, for example:
endo-2-[2-hydroxy-2-phenyl-2-(thien-3-yl)]acetoxy-7-methyl-7-azabicyclo[2.2.1]heptane methyl bromide, m.p. 259°–261°;
endo-2-(2-cyclopentyl-2-hydroxy-2-phenyl)acetoxy-7-methyl-7-azabicyclo[2.2.1]heptane methyl bromide, m.p. 205°–206°;
endo-2-[2-hydroxy-2-phenyl-2-(pyrrol-3-yl)]acetoxy-7-methyl-7-azabicyclo[2.2.1]heptane methyl bromide;
endo-2-(2-hydroxy-2,2-dicyclopentyl)acetoxy-7-methyl-7-azabicyclo[2.2.1]heptane methyl bromide;
endo-2-[2-hydroxy-2,2-bis(4-chlorophenyl)]acetoxy-7-methyl-7-azabicyclo[2.2.1]heptane methyl bromide;
endo-2-[2-hydroxy-2-phenyl-2-(thien-2-yl)]acetoxy-7-methyl-7-azabicyclo[2.2.1]heptane methyl bromide, m.p. 262° (dec);
endo-2-(2-cyclohexyl-2-hydroxy-2-phenyl)acetoxy-7-methyl-7-azabicyclo[2.2.1]heptane methyl bromide, m.p. 222°–223°;
endo-2-(2-hydroxy-2-isopropyl-2-phenyl)acetoxy-7-methyl-7-azabicyclo[2.2.1]heptane methyl bromide, m.p. 244°–246°;
endo-2-[2-hydroxy-2-phenyl-2-(cyclopent-2-enyl)]-acetoxy-7-methyl-7-azabicyclo[2.2.1]heptane methyl bromide;
exo-2-[2-hydroxy-2-phenyl-2-(4-chlorophenyl)]-acetoxy-7-methyl-7-azabicyclo[2.2.1]heptane methyl bromide;
exo-2-[2-hydroxy-2-phenyl-2-(thien-2-yl)]acetoxy-7-methyl-7-azabicyclo[2.2.1]heptane methyl bromide;
exo-2-[2-hydroxy-2-phenyl-2-(4-methylphenyl)]-acetoxy-7-methyl-7-azabicyclo[2.2.1]heptane methyl bromide;
exo-2-(2-hydroxy-2,2-diphenyl)acetoxy-7-methyl-7-azabicyclo-[2.2.1]heptane methyl bromide;
exo-2-[2-hydroxy-2-phenyl-2-(thien-3-yl)]acetoxy-7-methyl-7-azabicyclo[2.2.1]heptane methyl bromide;
exo-2-(2-cyclopentyl-2-hydroxy-2-phenyl)acetoxy-7-methyl-7-azabicyclo[2.2.1]heptane methyl bromide;
exo-2-(2-cyclohexyl-2-hydroxy-2-phenyl)acetoxy-7-methyl-7-azabicyclo[2.2.1]heptane methyl bromide; and
exo-2-(2-hydroxy-2-isopropyl-2-phenyl)acetoxy-7-methyl-7-azabicyclo[2.2.1]heptane methyl bromide.

EXAMPLE 3

A method for making an acid addition salt, exemplified by the hydrochloride salt, from the azabicycloheptyl glycolate is given in this example.

Etheral hydrogen chloride was added dropwise to a stirred solution of 2.0 g of endo-2-hydroxydiphenylacetoxy-7-methyl-7-azabicyclo[2.2.1]heptane in 20 ml of anhydrous ether until precipitation was complete. The product was filtered off, washed with ether, air dried and crystallized from methanol/ethyl acetate to yield endo-2-(2-hydroxy-2,2-diphenyl)acetoxy-7-methyl-7-azabicyclo[2.2.1]heptane hydrochloride, m.p. 270°–271°.

Proceeding in a similar manner, other subject compounds can be converted to their corresponding acid addition salt using the above procedure. There may be prepared, for example, the following compounds:
endo-2-[2-hydroxy-2-phenyl-2-(thien-3-yl)]acetoxy-7-methyl-7-azabicyclo[2.2.1]heptane hydrochloride;
endo-2-(2-cyclopentyl-2-hydroxy-2-phenyl)]acetoxy-7-methyl-7-azabicyclo[2.2.1]heptane hydrochloride;
endo-2-[2-hydroxy-2-phenyl-2-(thien-2-yl)]acetoxy-7-methyl-7-azabicyclo[2.2.1]heptane hydrochloride;
endo-2-(2-cyclohexyl-2-hydroxy-2-phenyl)acetoxy-7-methyl-7-azabicyclo[2.2.1]heptane hydrochloride;
endo-2-(2-hydroxy-2-isopropyl-2-phenyl)acetoxy-7-methyl-7-azabicyclo[2.2.1]heptane hydrochloride;
exo-2-(2-hydroxy-2,2-dimethyl)acetoxy-7-methyl-7-azabicyclo[2.2.1]heptane hydrochloride;
exo-2-[2-hydroxy-2-phenyl-2-(thien-2-yl)]acetoxy-7-methyl-7-azabicyclo[2.2.1]heptane hydrochloride; and
exo-2-[2-hydroxy-2-phenyl-2-(4-methylphenyl)]-acetoxy-7-methylazabicyclo[2.2.1]heptane hydrochloride.

EXAMPLE 4

This example illustrates the conversion of an acid addition salt to the corresponding free base.

Two grams of endo-2-(2-hydroxy-2,2-diphenyl-)acetoxy-7-methyl-7-azabicyclo[2.2.1]heptane hydrochloride in 50 ml of dichloromethane was shaken with excess dilute potassium carbonate solution until the salt was completely dissolved. The organic layer was separated, washed twice with water, dried over magnesium sulfate and evaporated to yield endo-2-(2-hydroxy-2,2-diphenyl)acetoxy-7-methyl-7-azabicyclo[2.2.1]heptane as an oil. In similar manner the acid salts of all compounds of formula 2 and 3 may be converted to the corresponding free base.

EXAMPLE 5

This example illustrates the process whereby a quaternary ammonium halide salt, exemplified by the bromide salt, of a compound of Example 2 is converted to the corresponding nitrate salt.

To a solution of 2 g of endo-2-(2-cyclopentyl-2-hydroxy-2-phenyl)acetoxy-7-methyl-7-azabicyclo[2.2.1]heptane methyl bromide in 50 ml of acetonitrile was added an equimolar solution of silver nitrate in 25 ml of acetonitrile with stirring. The product containing solvent was filtered off, evaporated to dryness and the residue crystallized from methanol/ethylacetate to afford endo-2-(2-cyclopentyl-2-phenyl)acetoxy-7-methyl-7-azabicyclo[2.2.1]heptane methyl nitrate.

Following the same procedure but substituting the appropriate bromide, chloride or iodide salt, all quaternary ammonium alkyl halide salts can be converted to the corresponding quaternary ammonium alkyl nitrate salt.

EXAMPLE 6

The following illustrates the preparation of representative pharmaceutical formulations which may be used for effecting bronchodilation utilizing an active compound such as endo-2-[2-hydroxy-2-phenyl-2-(thien-3-yl)]acetoxy-7-methyl-7-azabicyclo heptane methyl bromide.

| Inhalation Formulation | Amounts |
| --- | --- |
| Active compound | .1-15 wt/wt |
| Sorbitan trioleate | .025% wt/wt |
| Trichloromonofluoromethane | 35% wt/wt |
| Dichlorodifluoromethane | q.s. 100% |

The active compound, sorbitan trioleate and half of the trichloromonofluoromethane are mixed together. This mix is chilled to $-55°$ C. and the remainder of the trichloromonofluoromethane, followed by the dichlorodifluoromethane, is added. The final composition is placed in glass or metal vials which are sealed with metered dose valves.

While the present invention has been described with reference to specific embodiments thereof, it should be understood by those skilled in the art that various changes may be made and equivalents may be substituted without departing from the true spirit and scope of the invention. In addition, many modifications can be made to adapt a particular situation, material or composition of matter, process, process step or steps or objective to the spirit of this invention without departing from its central teaching.

What is claimed is:

1. A compound having the general formula

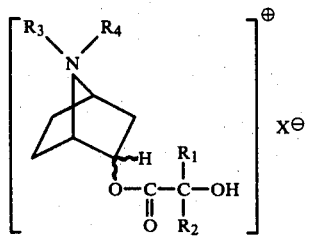

(1)

wherein the serrated lines denote both endo and exo forms;

$R_1$ and $R_2$ are the same or different and are $C_1$ to $C_6$ alkyl, $C_5$ or $C_6$ cycloalkyl, $C_5$ or $C_6$ cycloalkenyl, phenyl optionally substituted with $C_1$ to $C_6$ alkyl, $C_1$ to $C_6$ alkoxy or halo, or 5 or 6 membered heterocyclic aryl wherein the heteroatom is oxygen, nitrogen or sulfur;

$R_3$ is a $C_1$ to $C_6$ alkyl;

$R_4$ and X are optionally present, and when present $R_4$ is a $C_1$ to $C_6$ alkyl radical or hydrogen and X is an inorganic or organic anion which forms a pharmaceutically acceptable salt.

2. The compound of claim 1 wherein $R_1$ is phenyl optionally substituted with $C_1$ to $C_4$ alkyl, $C_1$ to $C_4$ alkoxy, chloro or bromo; $R_2$ is the same as $R_1$ or is $C_5$ to $C_6$ cycloalkyl or heterocyclic aryl wherein the heteroatom is sulfur; $R_3$ is a $C_1$ to $C_4$ alkyl; and $R_4$ and X are present, $R_4$ being a $C_1$ to $C_6$ alkyl or hydrogen and X is methanesulfonate, benzenesulfonate, chloride or bromide.

3. The compound of claim 2 wherein $R_1$ is phenyl; $R_2$ is phenyl, thienyl, cyclopentyl, cyclohexyl, or isopropyl; $R_3$ is methyl; $R_4$ is hydrogen or methyl; and X is bromide or chloride.

4. The compound of claim 3 which is endo-2-(2-hydroxy-2,2-diphenyl)acetoxy-7-methyl-7-azabicyclo[2.3.1]heptane hydrochloride.

5. The compound of claim 3 which is endo-2-(2-hydroxy-2,2-diphenyl)acetoxy-7-methyl-7-azabicyclo[2.2.1]heptane methyl bromide.

6. The compound of claim 3 which is endo-2-[2-hydroxy-2-phenyl-2-(thien-3-yl)]acetoxy-7-methyl-7-azabicyclo[2.2.1]heptane methyl bromide.

7. The compound of claim 3 which is endo-2-[2-hydroxy-2-phenyl-2-(thien-2-yl)]acetoxy-7-methyl-7-azabicyclo[2.2.1]heptane methyl bromide.

8. The compound of claim 3 which is endo-2-(2-cyclopentyl-2-hydroxy-2-phenyl)acetoxy-7-methyl-7-azabicyclo[2.2.1]heptane methyl bromide.

9. The compound of claim 3 which is endo-2-(2-cyclohexyl-2-hydroxy-2-phenyl-)acetoxy-7-methyl-7-azabicyclo[2.2.1]heptane methyl bromide.

10. The compound of claim 3 which is endo-2-(2-hydroxy-2-isopropyl-2-phenyl)acetoxy-7-methyl-7-azabicyclo[2.2.1]heptane methyl bromide.

11. A compound selected from the group consisting of those having the formulas (10), and (11)

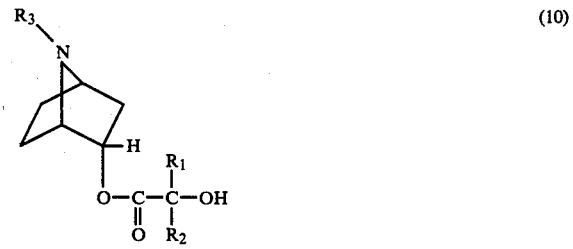

(10)

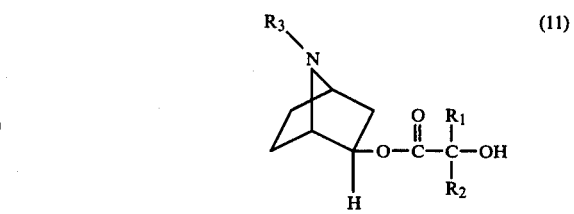

(11)

wherein $R_1$ and $R_2$ are the same or different and are $C_1$ to $C_6$ alkyl, $C_5$ to $C_6$ cycloalkyl, $C_5$ to $C_6$ cycloalkenyl, phenyl optionally substituted with $C_1$ to $C_6$ alkyl, $C_1$ to $C_6$ alkoxy or halo, or 5 or 6 membered heterocyclic aryl wherein the heteroatom is oxygen, nitrogen or sulfur; and $R_3$ is $C_1$ to $C_6$ alkyl.

12. An anticholinergic pharmaceutical composition which comprises a pharmaceutically acceptable carrier and a compound represented by the formula

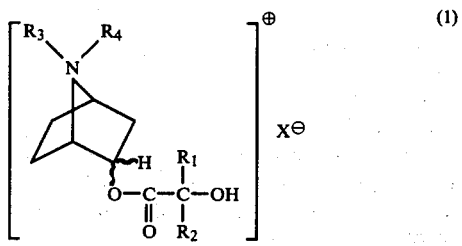

wherein the serrated lines denote both endo and exo forms;
$R_1$ and $R_2$ are the same or different and are $C_1$ to $C_6$ alkyl, $C_5$ or $C_6$ cycloalkyl, $C_5$ or $C_6$ cycloalkenyl, phenyl optionally substituted with $C_1$ to $C_6$ alkyl, $C_1$ to $C_6$ alkoxy or halo, or 5 or 6 membered heterocyclic aryl wherein the heteroatom is oxygen, nitrogen or sulfur;
$R_3$ is a $C_1$ to $C_6$ alkyl;
$R_4$ and X are optionally present, and when present $R_4$ is a $C_1$ to $C_6$ alkyl radical or hydrogen and X is an inorganic or organic anion which forms a pharmaceutically acceptable salt.

13. A method for effecting bronchodilation in mammals which comprises administering to a mammal a bronchodilating effective amount of a compound of the formula

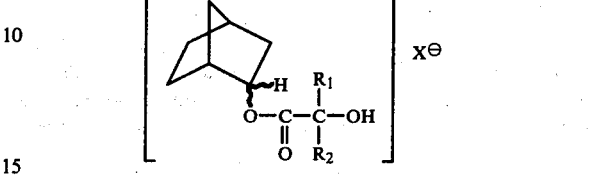

wherein the serrated lines denote both endo and exo forms;
$R_1$ and $R_2$ are the same or different and are $C_1$ to $C_6$ alkyl, $C_5$ or $C_6$ cycloalkyl, $C_5$ or $C_6$ cycloalkenyl, phenyl optionally substituted with $C_1$ to $C_6$ alkyl, $C_1$ to $C_6$ alkoxy or halo, or 5 or 6 membered heterocyclic aryl wherein the heteroatom is oxygen, nitrogen or sulfur;
$R_3$ is a $C_1$ to $C_6$ alkyl;
$R_4$ and X are optionally present, and when present $R_4$ is a $C_1$ to $C_6$ alkyl radical or hydrogen and X is an inorganic or organic anion which forms a pharmaceutically acceptable salt.

* * * * *